United States Patent [19]

Elsner et al.

[11] 4,163,760

[45] Aug. 7, 1979

[54] CONTINUOUS PRODUCTION OF ORGANIC PHOSPHINES

[75] Inventors: Georg Elsner, Hürth; Gero Heymer, Erftstadt; Hans-Werner Stephan, Cologne, all of Fed. Rep. of Germany

[73] Assignee: Hoechst Aktiengesellschaft, Hürth Knapsack, Fed. Rep. of Germany

[21] Appl. No.: 872,250

[22] Filed: Jan. 25, 1978

[30] Foreign Application Priority Data

Jan. 29, 1977 [DE] Fed. Rep. of Germany ....... 2703802

[51] Int. Cl.$^2$ ................................................ C07F 9/54
[52] U.S. Cl. ............................................. 260/606.5 P
[58] Field of Search .................................. 260/606.5 P

[56] References Cited

U.S. PATENT DOCUMENTS

| | | | |
|---|---|---|---|
| 2,584,112 | 2/1952 | Brown | 260/606.5 P |
| 2,803,597 | 8/1957 | Stiles et al. | 260/606.5 P X |
| 2,822,376 | 2/1958 | Hechenbleikner et al. | 260/606.5 P X |
| 2,957,931 | 10/1960 | Hamilton et al. | 260/606.5 P X |
| 3,400,163 | 9/1968 | Mason et al. | 260/606.5 P |
| 3,401,204 | 9/1968 | Mason et al. | 260/606.5 P |
| 3,435,076 | 3/1969 | Mason | 260/606.5 P |

*Primary Examiner*—Helen M. S. Sneed
*Attorney, Agent, or Firm*—Connolly and Hutz

[57] ABSTRACT

Organic phosphines are produced by reacting an alkylene, cycloalkylene or aralkylene in the presence of a free radical-yielding catalyst. More specifically, a pressure reactor, which is provided in its interior with mixing elements, kept free from oxygen, and subdivided so as to comprise an upper cooling zone and a lower reaction zone, is continuously supplied from above with (a) a solution of the alkylene, cycloalkylene or aralkylene and the catalyst in an inert solvent, and (b) a stoichiometric excess of hydrogen phosphide, the said (a) and (b) reactants being supplied jointly with but separately from one another; the (a) and (b) reactants are mixed in the upper cooling zone of the reactor at about 0° to 35° C. and under a PH$_3$-pressure of about 80 to 300 bars; the resulting mixture, which travels downwardly in the reactor, is reacted in the lower reaction zone at about 90° to 190° C., the reactants being allowed to remain in the reactor for a period of time about 13 to 15 times longer than the half life period of the catalyst; the reaction mixture is removed through the bottom portion of the reactor and subjected to distillation so as to separate the organic phosphines.

12 Claims, 1 Drawing Figure

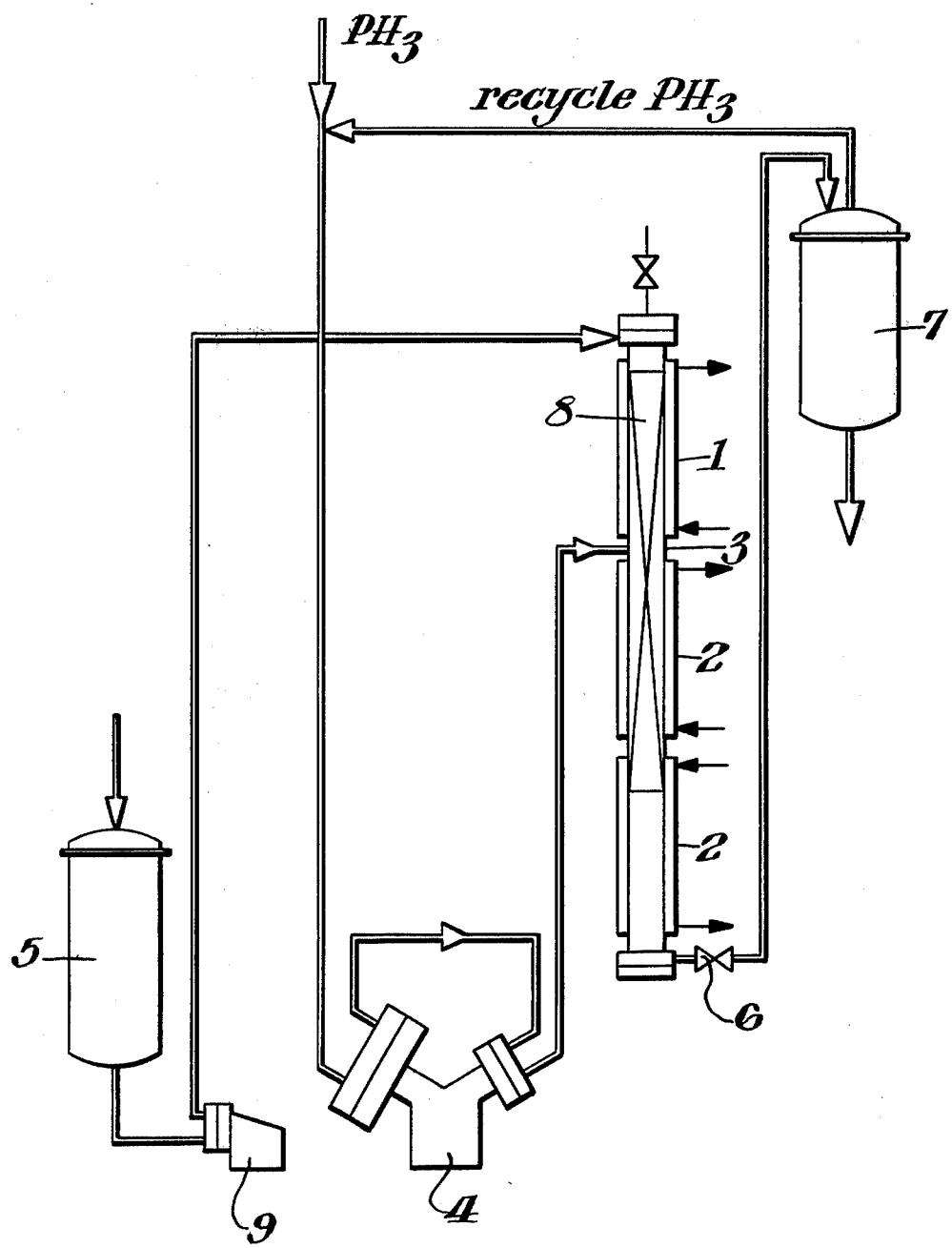

CONTINUOUS PRODUCTION OF ORGANIC PHOSPHINES

This invention relates to a process for the continuous manufacture of organic phosphines of the following general formula (I) or (II)

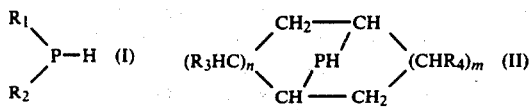

in which formula (I) $R_1$ and $R_2$ each stand for an alkyl-, cycloalkyl- or aralkyl group having 2 to 18 carbon atoms or one of the substituents $R_1$ and $R_2$ stands for a hydrogen atom and the other stands for one of the said groups, and in which formula (II) m and n each stand for 1, 2 or 3, the sum of m+n being at most 5, and $R_3$ and $R_4$, being identical or different, each stand for a hydrogen atom or an alkyl group having 2 to 6 carbon atoms.

German Patent Specification No. 899,040 describes a process, wherein hydrogen phosphide is reacted with an equivalent proportion of an olefin at elevated temperature in the presence of a peroxidic catalyst with the resultant formation (cf. Example 2 in that patent specification) of a mixture consisting approximately of 85 weight % of trialkylphosphine and 15 weight % of mono- or dialkylphosphine.

A further process, wherein a stoichiometric excess of hydrogen phosphide, namely 3.6 mols of $PH_3$, is reacted with 1 mol of 1-octene over a period of 6 hours, is referred to in Journal of Organic Chemistry (1961), vol 26, page 5139, Table II. As disclosed in this literature reference, it is possible by the use of a stoichiometric excess of $PH_3$ to influence the composition of the resulting reaction mixture in such a manner that the formation of monooctylphosphine tends to be favored over that of dioctylphosphine and trioctylphosphine up to a monooctylphosphine yield of 75%. Despite such improved yield of monooctylphosphine, the process just described is not fully satisfactory as long periods of time are needed to terminate the reaction.

A still further process, wherein hydrogen phosphide is additively combined with 1,5-cyclooctadiene in the presence of azobisisobutyronitrile with the resultant formation of an isomeric mixture of 9-phosphabicyclo-[4.2.1.]-nonane and 9-phosphabicyclo-[3.3.1.]-nonane has been described in German Patent Specification "Offenlegungsschrift" No. 1,909,620, Example 1). As described therein, this additive reaction was carried out as follows: A pressure vessel was fed with molar proportions of 1,5-cyclooctadiene and hydrogen phosphide and the reaction was started by the addition of azobisisobutyronitrile and by gradually heating the starting mixture to 75° C., which gave rise to a pressure increase to 19.3 atmospheres, in the pressure vessel. After 20 minutes, the temperature increased to 85° C. and the pressure dropped to 8.1 atmospheres. The reaction was terminated after the reaction mixture had been heated for a further 12 hours to 75° C., and the above mixture of isomers was obtained in a yield of 57%.

This unsatisfactory yield appears to indicate that the secondary phosphine is obtained together with tertiary phosphine as an undesirable by-product, which adversely affects the economy of this known process.

It is therefore an object of the present invention to provide a process which is free from the disadvantageous phenomena described above and which permits primary and secondary organic phosphines to be produced continuously in good yields. To this end, the invention provides for hydrogen phosphide to be reacted with an olefin in the presence of a catalyst at temperatures and under pressures higher than those employed in the processes described heretofore.

The present invention relates more particularly to an improved process for the continuous production of organic phosphines of the following general formula (I) or (II)

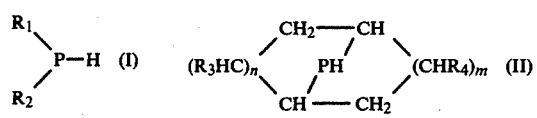

in which formula (I) $R_1$ and $R_2$ each stand for an alkyl-, cycloalkyl- or aralkyl group having 2 to 18 carbon atoms, or one of the substituents $R_1$ and $R_2$ stands for a hydrogen atom and the other stands for one of the said groups, and in which formula (II) m and n each stand for 1, 2 or 3, the sum of m+n being at most 5, and $R_3$ and $R_4$, being identical or different, each stand for a hydrogen atom or an alkyl group having 1 to 6 carbon atoms, wherein the formula (I) compound is made by reacting an alkylene, cycloalkylene or aralkylene having 2 to 18 carbon atoms with hydrogen phosphide, or the formula (II) compound is made by reacting a compound of the following general formula (III)

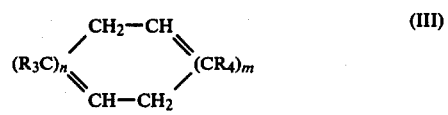

in which m, n, $R_3$ and $R_4$ have the meanings given above, with hydrogen phosphide at elevated temperature and under elevated pressure in the presence of a free radical-yielding catalyst solution in an inert solvent, terminating the reaction and separating the resulting organic phosphine from the reaction mixture, the improved process comprising: continuously supplying from above a pressure reactor, which is provided in its interior with mixing elements, kept free from oxygen, and subdivided so as to comprise an upper cooling zone and a lower reaction zone, with (a) a solution of the alkylene, cycloalkylene or aralkylene or of a compound of general formula (III) and the catalyst in an inert solvent, and (b) a stoichiometric excess of hydrogen phosphide, the said (a) and (b) reactants being supplied jointly with but separately from one another; mixing the said (a) and (b) reactants in the upper cooling zone of the reactor at a temperature of about 0° to 35° C. and under a $PH_3$-pressure of about 80 to 300 bars; reacting the resulting mixture, which travels downwardly in the reactor, in the lower reaction zone at about 90° to 190° C., the reactants being allowed to remain in the reactor for a period of time about 13 to 15 times longer than the half life period of the catalyst; removing the reaction mixture through the bottom portion of the reactor and, after pressure release to atmospheric, subjecting the mixture to distillation so as to separate the organic phosphines therefrom.

The olefinic reactants, which are preferably used in the process of this invention, comprise alkylenes having 2 to 18 carbon atoms or cycloalkylenes, aralkylenes or compounds of the above general formula (III) having 6 to 9 carbon atoms, especially 1-octene, cyclohexane or cyclooctadiene-1.5.

It is also advantageous to dissolve the olefinic reactant and catalyst in a solvent, such as hexane, benzene or toluene, for example, the solvent and olefinic reactant being preferably employed in a quantitative ratio of 1:1 and the catalyst being used in a proportion of about 0.1 to 5 mol %, based on the quantity of the alkylene, cycloalkylene or aralkylene or compound of general formula (III). The catalysts, which are suitable for use in the present reaction, are known in the art and may be selected from perioxidic radical-yielding agents or azobis-isobutyronitrile.

In order to thoroughly mix the solution containing the catalyst and olefinic reactant with the hydrogen phosphide, it is good practice to operate the cooling zone of the reactor at a sufficiently low temperature, preferably to 20° to 30° C., and under a $PH_3$-pressure in the reactor of 120 to 180 bars, at which the hydrogen phosphide in that zone is in the liquid state. The reactants can be mixed together, e.g. with the help of packing material placed in the reactor, or other suitable mixing means.

A further preferred feature of the present process provides for the reaction zone to be maintained at a temperature of 110° to 130° C. Under the conditions prevailing in the reaction zone, the hydrogen phosphide undergoes evaporation and rapid reaction with the olefinic reactant. The reactant mixture is allowed to remain in the reactor over a period of time which, for example, may be 13 to 15 times longer than the half life period of the catalyst, and can then be removed through the bottom portion of the reactor. Unreacted hydrogen phosphide in excess, which is set free upon releasing the pressure to atmospheric, and the mixture of solvent and unreacted olefinic reactant, which is recovered on subjecting the reaction mixture to distillation, may be recycled to the reactor.

In carrying out the process of the present invention, use may, for example, be made of a high pressure reactor, of which the upper portion is provided with a cooling jacket and of which the lower portion is provided with a heating jacket, the ratio of reactor diameter to reactor height being 1:50 to 1:200. By the selection of a larger reactor diameter, it is possible to increase the throughput capacity, and by the selection of a greater reactor height, it is possible to prolong the residence time of the reaction mixture in the reactor. Any known technical aids, such as a compressor, a pump or timed outlet valve, may be used for introducing the reactants into the reactor from above and for removing the reaction mixture through the bottom portion of the reactor. It is finally possible to mix the reactants inside the reactor by means of filler material which is placed therein.

The following statements are intended further to illustrate the process of the present invention.

The entire apparatus is carefully scavenged with nitrogen. Next, the tubular reactor is charged with hydrogen phosphide up to the final pressure of the compressor, which should be at least 80 bars. Following this, the lower portion of the reactor is heated by means of steam or hot water, and the upper portion of the reactor is cooled with the aid of cooling water. Next, a prepared reaction solution consisting of an olefin, which is liquid at room temperature or sufficiently soluble in the inert solvent, the inert solvent and the radical-yielding initiator, is injected into the head portion of the reactor by means of a dosing pump. In the upper cooled portion of the reactor, the reaction solution is mixed with hydrogen phosphide. The resulting mixture flows gradually downward under the action of gravity into the heated portion of the reactor, in which it undergoes complete reaction. The heated lower portion of the reactor is maintained at the temperature at which the radical initiator is decomposed to an extent of more than 99.99%, for a preselected residence time. The reaction mixture is removed through the bottom portion of the reactor and processed. More specifically, the inert solvent is distilled off and the remaining residue is either distilled or crystallized, depending on the particular physical properties of the phosphine made.

The present process compares favorably with the prior art methods in respect of the following points: It enables the space/time-yield to be improved, ensures high conversion rates in the absence of side reactions, and permits continuous operation.

The products of the present invention are valuable intermediates for the production of catalysts for use in hydroformylation reactions.

The invention will now be described with reference to the single FIGURE diagrammatic flow sheet of the drawing illustrating by way of example a preferred embodiment of the present invention.

EXAMPLE 1

Hydrogen phosphide was introduced by means of a membrane compressor (4) into a high pressure reactor (3), 2 cm wide and 250 cm high and charged with fillers (8), of which the upper portion was provided with a cooling jacket (1) and of which the lower portion was provided with a heating jacket (2). The lower heating jacket (2) was heated to 120° C. by means of steam and the upper cooling jacket (1) was cooled to about 25° C. by means of fresh water. A pressure of 150 bars established in the reactor (3). A solution containing cyclohexene, toluene and azobis-isobutyronitrile in a quantitative ratio of 50:50:1 coming from a receiver (5) was pumped with the pump (9) into the reactor (3). After the introduction of about 300 ml of solution, the outlet valve (6) in the bottom portion of the reactor (3) was opened. By appropriately selecting the opening time and opening width of the valve (6), it was ensured that the quantity of reaction mixture removed corresponded substantially to the quantity of feed solution. In this manner, about 1 liter/h of the above solution was conveyed through the reactor (3). Downstream of the outlet valve (6), the solution was delivered with pressure release to a container (7), freed from dissolved $PH_3$ and analyzed by NMR-spectroscopy. It was found that exclusively primary cyclohexylphosphine had been formed. ($^{31}p$: doublet at +110 and 121 ppm converted to 85% $H_3PO_4$ as external standard). The $^1H$-NMR-spectrum indicated a 70% conversion rate of the cyclohexene used.

EXAMPLE 2

The procedure was as in Example 1, but a mixture of n-octene-(1), toluene and azobisisobutyronitrile was pumped into the reactor. The resulting product was analyzed by NMR-spectroscopy. The octene conversion rate was 70% and primary 1-octylphosphine was obtained in a yield of 80%, based on the octene which underwent conversion.

EXAMPLE 3

The procedure was as in Example 1, but a mixture of cyclooctadiene-(1,5), toluene and azobisisobutyronitrile was pumped into the reactor. The reaction mixture was analyzed by gas chromatography and found to have the following quantitative composition:

| | |
|---|---|
| Toluene | 50.5 weight % |
| 9H-9-phosphabicyclononane (an isomeric mixture of 3.3.1- and 4.2.1-nonanes) | 43.9 weight % |
| cyclooctadiene-(1,5) | 4.1 weight % |
| tertiary phosphine (4 isomers) | 1.5 weight % |

This corresponded to a 90% conversion rate of the cyclooctadiene-(1,5) and to a 96% yield of desirable secondary phosphine, based on the quantity of cyclooctadiene.

EXAMPLE 4

(Comparative Example)

A 1-liter autoclave was charged with 5 g of azobisisobutyronitrile, 50 g (1 mol) of benzene and 108 g (1 mol) of 1,5-cyclooctadiene and 34 g (1 mol) of $PH_3$ was condensed thereinto. Next, the mixture was cautiously heated to 80° C. with pressure increase to 18 bars. The reaction commenced starting after an induction period of 1 hour with a slight temperature increase to 90° C. The pressure dropped within 12 hours to 6 bars.

The reaction mixture was analyzed by gas chromtagraphy and the following result was obtained:

7 weight % of cyclooctadiene-1,5
20 weight % of tertiary phosphine (4 isomers)
49 weight % of 9H-9-phosphabicyclononane (an isomeric mixture of 3.3.1- and 4.2.1-nonanes)
24 weight % benzene.

EXAMPLE 5

(Comparative Example)

A 1-liter autoclave was charged with 5 g of azobisisobutyronitrile, 50 g of benzene and 82 g (1 mol) of cyclohexene, and 68 g (2 mols) of hydrogen phosphide was condensed thereinto. The whole was heated to 85° C. The pressure initially rose to 40 bars, then dropped gradually to 25 bars, and remained constant after 6 hours. The reaction mixture was analyzed by NMR-spectroscopy. The cyclohexene conversion rate was 78 weight %. Primary cyclohexylphosphine was obtained in a yield of 60% and secondary cyclohexylphosphine was obtained in a yield of 40%, based on the cyclohexene which underwent conversion.

EXAMPLE 6

(Comparative Example)

A 1-liter autoclave was charged with 5 g of azobisisobutyronitrile, 50 g of benzene and 112 g (1 mol) of 1-octene, and 136 g (4 mols) of hydrogen phosphide was condensed thereinto. The whole was heated to 90° C. The pressure initially rose to 70 bars, then dropped gradually to 55 bars, and remained constant after 5 hours. The reaction mixture was analyzed by NMR-spectroscopy. The octene conversion rate was 85%. Primary octylphosphine was obtained in a yield of 70%, secondary octylphosphine was obtained in a yield of 20%, and tertiary octylphosphine was obtained in a yield at 10%, based on the quantity of 1-octene which underwent conversion.

We claim:

1. In a process for the continuous production of organic phosphines of the following general formula (I) or (II)

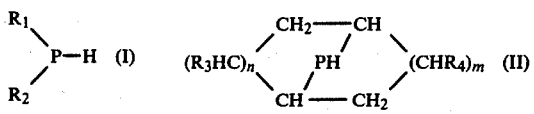

in which formula (I) $R_1$ and $R_2$ each are selected from the group consisting of an alkyl-, cycloalkyl- or aralkyl group having 2 to 18 carbon atoms, or one of the substituents $R_1$ and $R_2$ is a hydrogen atom and the other is one of the said groups, and in which formula (II) m and n each are 1, 2 or 3, the sum of m+n being at most 5, and $R_3$ and $R_4$, being identical or different, each are a hydrogen atom or an alkyl group having 1 to 6 carbon atoms, wherein the formula (I) compound is made by reacting an alkylene, cycloalkylene or aralkylene having 2 to 18 carbon atoms with hydrogen phosphide, or the formula (II) compound is made by reacting a compound of the following general formula (III)

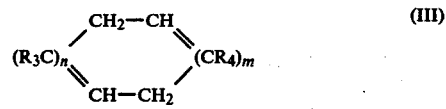

in which m, n, $R_3$ and $R_4$ have the meanings given above, with hydrogen phosphide at elevated temperature and under elevated pressure in the presence of a free radical-yielding catalyst solution in an inert solvent, terminating the reaction and separating the resulting organic phosphine from the reaction mixture, the improvement which comprises: continuously supplying from above a pressure reactor, which is provided in its interior with mixing elements, kept free from oxygen, and subdivided so as to comprise an upper cooling zone and a lower reaction zone, with (a) a solution of the alkylene, cycloalkylene or aralkylene or of a compound of general formula (III) and the catalyst in an inert solvent, and (b) a stoichiometric excess of hydrogen phosphide, the said (a) and (b) reactants being supplied jointly with, but separately from, one another; mixing the said (a) and (b) reactants in the upper cooling zone of the reactor at a temperature of about 0° to 35° C. and under a $PH_3$-pressure of about 80 to 300 bars; reacting the resulting mixture, which travels downwardly in the reactor, in the lower reaction zone at about 90° to 190° C., the reactants being allowed to remain in the reactor for a period of time about 13 to 15 times longer than the half life period of the catalyst; removing the reaction mixture through the bottom portion of the reactor and, after pressure release to atmospheric, subjecting the mixture to distillation so as to separate the organic phosphines therefrom.

2. The process as claimed in claim 1, wherein the alkylene contains 2 to 18 carbon atoms.

3. The process as claimed in claim 1, wherein the cycloalkylene, aralkylene or the compound of general formula (III) contains 6 to 9 carbon atoms.

4. The process as claimed in claim 1, wherein 1-octene, cyclohexene or cyclooctadiene-1,5 is reacted with hydrogen phosphide.

5. The process as claimed in claim 1, wherein azobisisobutyronitrile or a peroxidic radical-yielding agent is used as the catalyst.

6. The process as claimed in claim 1, wherein hexane, benzene or toluene is used as the solvent.

7. The process as claimed in claim 1, wherein the catalyst is used in a proportion of about 0.5 to 5 mol %, based on the quantity of the alkylene, cycloalkylene, aralkylene or compound of general formula (III).

8. The process as claimed in claim 1, wherein the upper cooling zone of the reactor is maintained at a temperature of 20° to 30° C. and the lower reaction zone of the reactor is maintained at a temperature of 110° to 130° C.

9. The process as claimed in claim 1, wherein a $PH_3$-pressure of 120 to 180 bars is maintained in the reactor.

10. The process as claimed in claim 1, wherein the reactants are allowed to remain in the reactor for a period of time which is 13 to 15 times longer than the half life period of the catalyst.

11. The process as claimed in claim 1, wherein the solvent and olefinic reactant are used in a quantitative ratio of 1:1.

12. The process as claimed in claim 1, wherein hydrogen phosphide which is set free upon subjecting the reaction mixture to pressure release to atmospheric, and the mixture of solvent and unreacted olefinic reactant which is recovered on subjecting the reaction mixture to distillation, are recycled to the reactor.

* * * * *

UNITED STATES PATENT AND TRADEMARK OFFICE
CERTIFICATE OF CORRECTION

PATENT NO. : 4,163,760
DATED : August 7, 1979
INVENTOR(S) : Elsner et al

It is certified that error appears in the above-identified patent and that said Letters Patent are hereby corrected as shown below:

COVER PAGE, left-hand column, item "[73] Assignee:"

change "Hurth Knapsack" to --Frankfurt/Main--.

Signed and Sealed this

Twenty-ninth Day of April 1980

[SEAL]

Attest:

SIDNEY A. DIAMOND

Attesting Officer

Commissioner of Patents and Trademarks